(12) United States Patent
Shen

(10) Patent No.: US 6,428,475 B1
(45) Date of Patent: Aug. 6, 2002

(54) MOBILE PHONE COMBINED PHYSIOLOGICAL FUNCTION DETECTOR

(76) Inventor: Ein-Yiao Shen, 5F, No. 8, Lane 132, Sec.2, Da-An Rd., Taipei (TW)

( * ) Notice: Subject to any disclaimer, the term of this patent is extended or adjusted under 35 U.S.C. 154(b) by 0 days.

(21) Appl. No.: 09/472,283

(22) Filed: Dec. 27, 1999

(51) Int. Cl.[7] .................................................. A61B 5/00
(52) U.S. Cl. ...................................... 600/300; 128/903
(58) Field of Search ................................. 600/300, 301, 600/500, 509, 513, 523, 483; 128/903, 904

(56) References Cited

U.S. PATENT DOCUMENTS

| | | | | |
|---|---|---|---|---|
| 5,544,661 A | * | 8/1996 | Davis et al. ................. | 128/904 |
| 5,720,770 A | * | 2/1998 | Nappholz et al. ............. | 607/30 |
| 5,772,586 A | * | 6/1998 | Heinonen et al. ............ | 600/300 |
| 6,149,602 A | * | 11/2000 | Arcelus ....................... | 600/523 |

* cited by examiner

*Primary Examiner*—George R. Evanisko
(74) *Attorney, Agent, or Firm*—Raymond Y. Chan; David and Raymond Patent Group

(57) ABSTRACT

A mobile phone combined physiological function detector comprises: a physiological function signal receivable mobile phone set, a measurer used to touch on the human skin and transmit detection signals to the mobile phone set by wire or wireless transmission method. A communication and a detection function are existed concurrently in the mobile phone set that can show measured data in its display for reminding a user of his health conditions in addition to communication purpose to fully use the resources.

1 Claim, 5 Drawing Sheets

MOBILE PHONE COMBINED PHYSIOLOGICAL FUNCTION DETECTOR

BACKGROUND OF THE PRESENT INVENTION

1. Field of Invention

The present invention relates to a detector, and particularly to a mobile phone detector that combines with a mobile phone set for displaying personal physiological signals, such as blood pressure, pulse, heartbeat, etc.

2. Description of Related Arts

Looking back into the late few years, it is indisputable that the mobile phone was the favorite to most people all over the world. In addition, for communication function, the mobile phone also provides some extra functions that would seem fantastic a decade ago, such as Infrared Ray (IR) data transmission, Global Positioning System (GPS) for security purpose, Internet linkage, etc. The growth rate of the number of the consumer of the mobile phone doesn't seem even a little bit retarded. On the contrary, the upthrust reaches an amazing of two hundred thousand people per day according to newspapers. The mobile phone will inevitably become one of the indispensable personal stand equipments sooner or later.

However, recently, some experts have doubted the safety of the mobile phone due to its electromagnetic wave that may impair people's brains. Hence, manufacturers are focusing this pending exemplified problem and trying to find out a proper way to eliminate the electromagnetic wave including reduction of emission power. Under this atmosphere, the present invention has been brewed in consideration of combining a physiological detection device with a mobile phone set so that the detected results can be shown on the small display of the mobile phone set.

SUMMARY OF THE PRESENT INVENTION

The main object of the present invention is to provide a mobile phone combined physiological function detector, wherein a display of a mobile phone set is used concurrently for showing personal blood pressure, pulse, and etc., which are measured by an electronic measurer, in addition to the telecommunication.

Another object of the present invention is to provide a mobile phone combined physiological function detector corporated with an externally coupled measurer, wherein measured physical data, such as blood pressure or pulse, can be transmitted to an input terminal of a mobile phone set by wire or wireless transmission method.

A further object of the present invention is to provide a mobile phone combined physiological function detector which shows measured physical data on a display of a mobile phone set to fully use the resources.

In order to accomplish the above objects, the present invention provides a mobile phone combined physiological function detector which comprises: a physiological is function signal receivable mobile phone set, a measurer used to touch on a human skin and transmit detection signals to the mobile phone set by means of a wire or wireless transmission method, a sensor provided to the measurer for touch-sensing purpose. The sensed signals are transmitted via a conversion circuit and an output interface while the mobile phone set is switched to a signal-receiving module for receiving and showing the signals in the display of the mobile phone set in a dot-matrix array.

BRIEF DESCRIPTION OF THE DRAWINGS

For a better understanding to the present invention, together with further advantages or features thereof, a preferred embodiment is elucidated below with reference to the annexed drawings in which.

DETAILED DESCRIPTION OF THE PREFERRED EMBODIMENT

Figure 1:
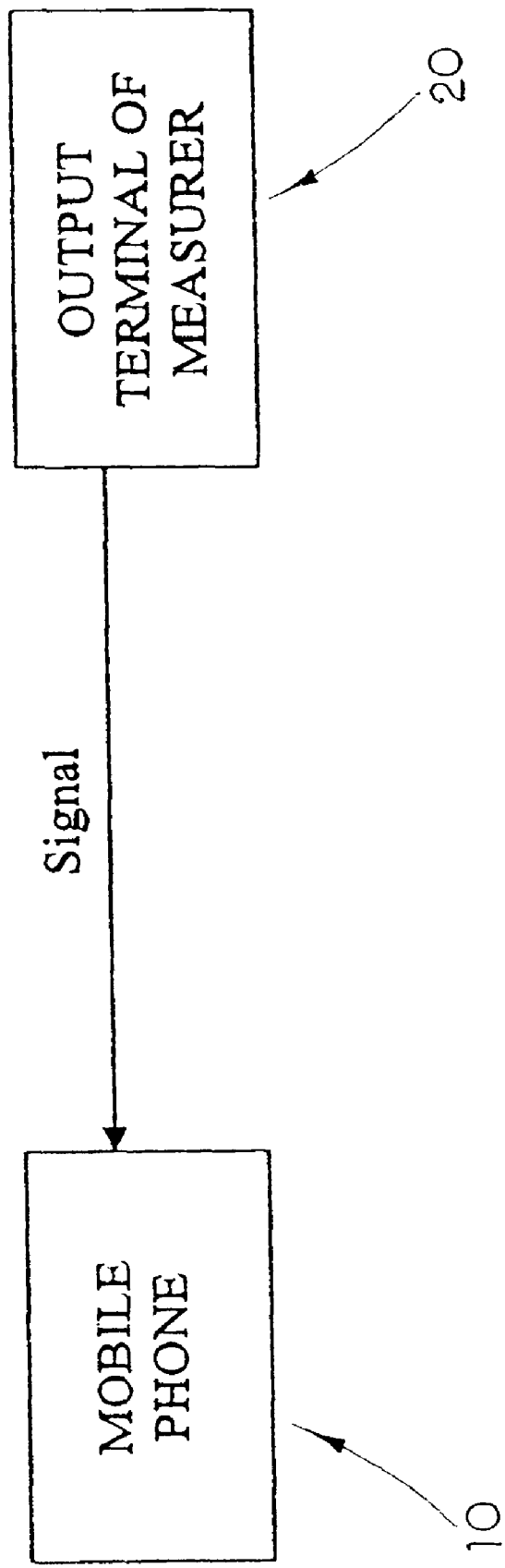
FIG. 1 is a signal transmission scheme of a mobile phone combined physiological function detector of the present invention.

As shown in FIG. 1, a mobile phone combined physiological function detector comprises a physiological function signal receivable mobile phone set 10 and a measurer 20 which is used to touch on a human skin and emit detected signals to the mobile phone set by means of a wire or wireless transmission method. The signal transmission method includes a direct connection of the output terminal of the measurer 20 to the input terminal of the mobile phone 10 or in a wireless form. The data obtained, such as blood pressure, pulse, and etc., will be shown in a display 12 of the mobile phone set 10 for using the latter in multi-purpose.

Figure 4A:
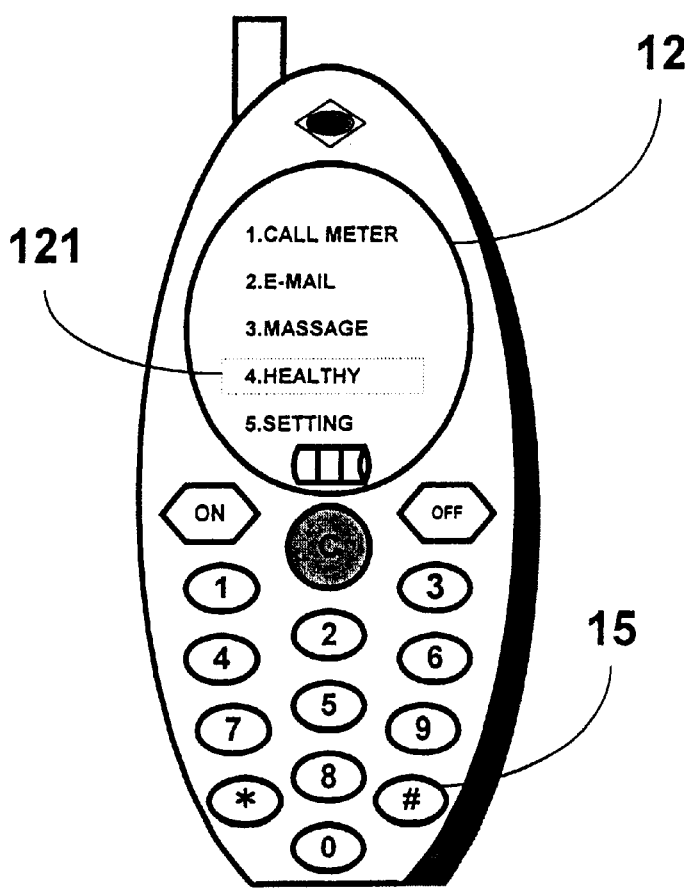
FIGS. 4A and 4B are schematic views showing a pull-down selection sheet respectively for function selection shown in the display of the mobile phone set.
Figure 4B:
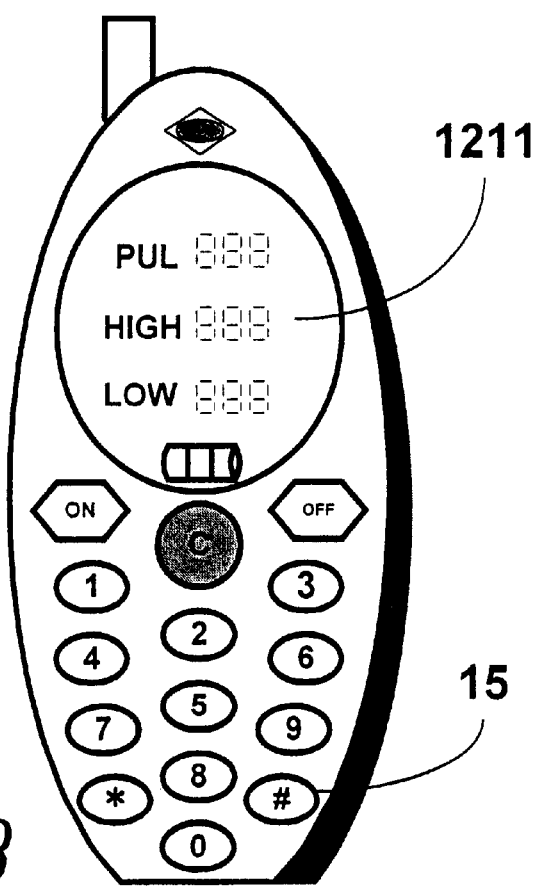

In operation an average mobile phone set, a pull-down selection sheet for function selection is usually adopted as shown in FIG. 4A. A "HEALTHY" function item 121 is added to the selection sheet of the present invention for entering a measuring mode 1211 shown in FIG. 4B. When the "HEALTHY" function key is selected, the mobile phone set enters a stand-by state to catch a signal from the measurer 20 and shows it in the display. For starting an air-filling valve, a user can press a pushbutton # or *—a preset start switch 15.

Figure 2:
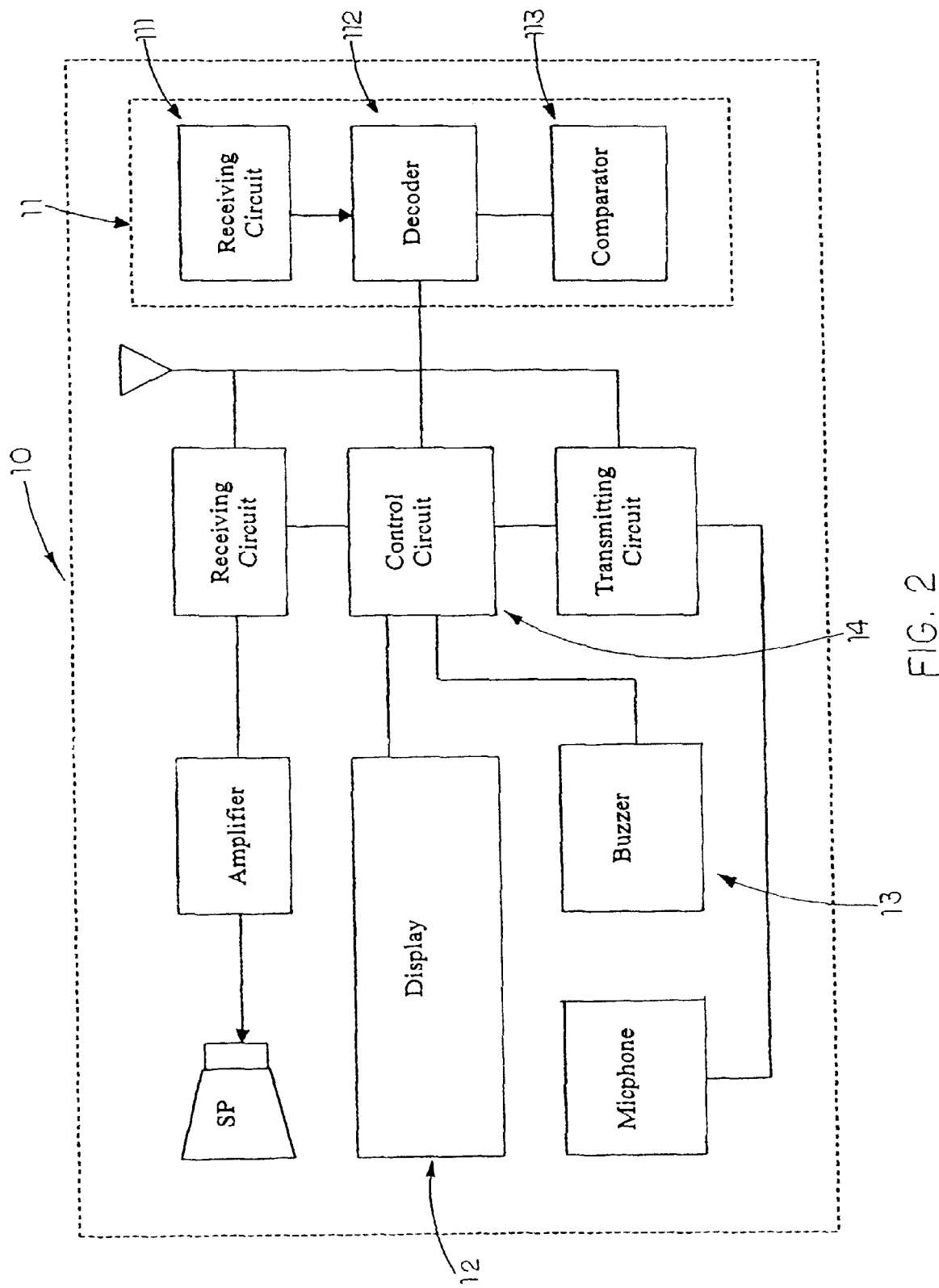
FIG. 2 is a block diagram of an extra signal-receiving device arranged in a mobile phone set.
Figure 3:
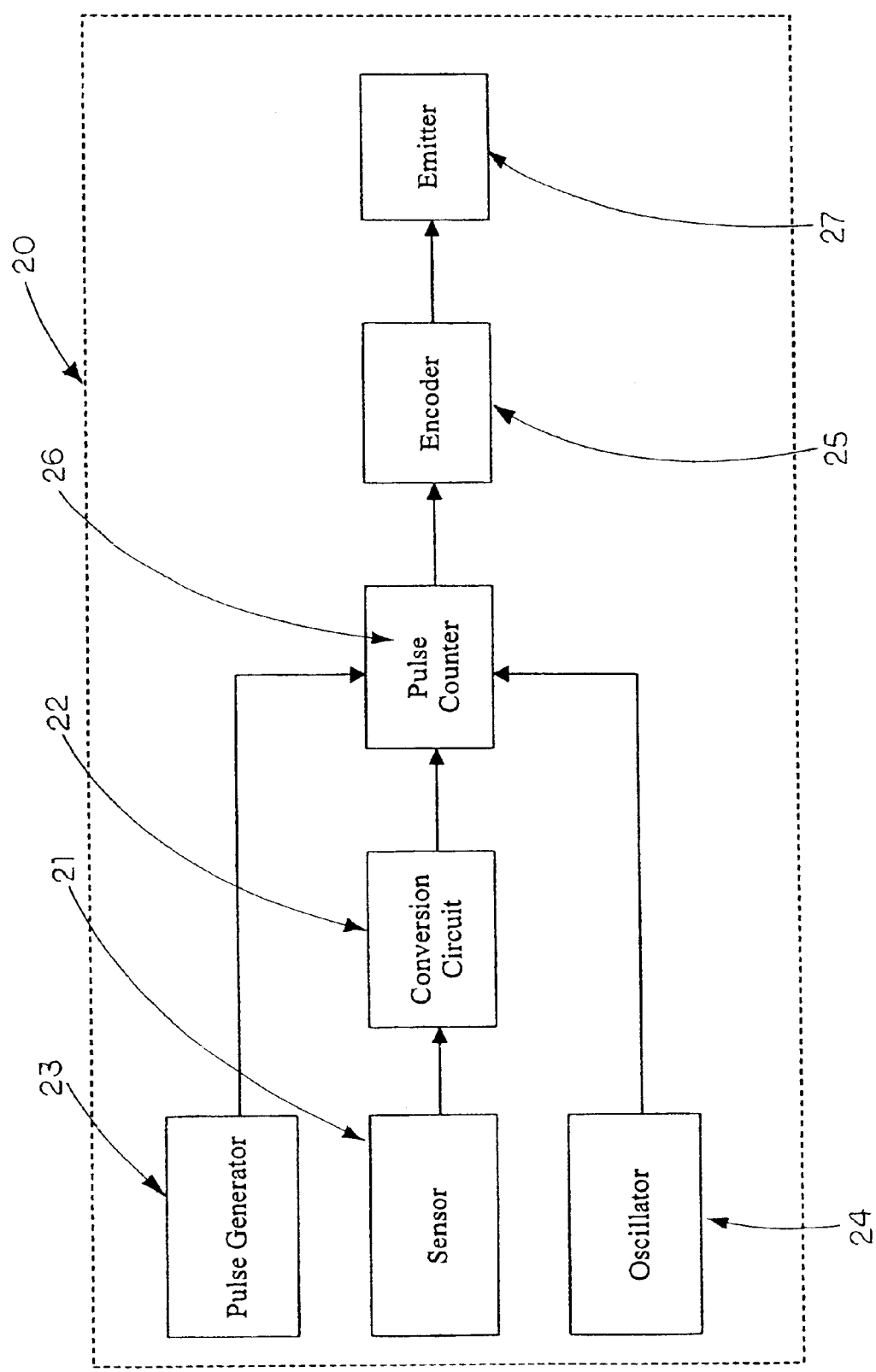
FIG. 3 is a block diagram showing a measurer used to touch and sense the human skin for emission of measured signals.

Referring to FIG. 2, a receiving module 11 is arranged in the mobile phone set 10, in addition to the basic communication circuit, for receiving the signals from the measurer 20. The receiving module 11 comprises a receiving circuit 111, a decoder 112, and a comparator 113. When the mobile phone set 10 enters the measuring mode, the receiving circuit 111 is ready for receiving signal from the measurer 20 and then the received signal is decoded by the decoder 112 and compared with a standard level of the comparator 113. When the measured value outruns the healthy value, a control circuit 14 will be triggered to drive a buzzer 13 alarming intermittently and showing the measured value in the display 12 for alerting a user of his health conditions. If an external phone call is effective during measuring, this device will ring or vibrate in multiplex operations to alert the user whether he would choose to continue the measurement or to answer the phone call alternatively.

Figure 5A:
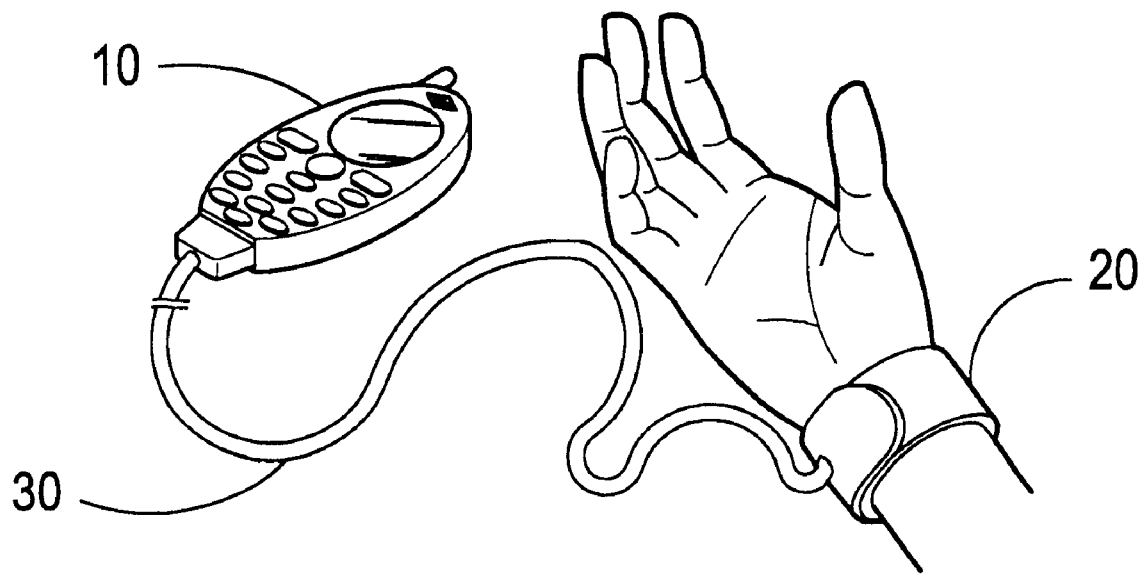
FIGS. 5A and 5B are schematic views showing signal transmission of the measurer in different ways.

Moreover, a set of Velcro fasteners is applied to the measurer 20 (FIG. 5A). An air sac (not shown) of the measurer 20 is used to accommodate compressed air so that excess thereof will be leaked out through a leakage valve (not shown) when the air sac is saturated. A sensor 21 is utilized to touch on the human skin for sensing pressure or beats, and the sensed signal will be converted through a conversion circuit 22, a pulse generator 23 and an oscillator 24 into an electric signal, which is then compared in a pulse counter 26 and coded in an encoder 25. Finally, it is emitted by an emitter 27. Further, by revising the measurer 20 to become a terminal measuring device, the present invention is also applicable in measuring some other extended healthy indices, such as concentration of blood oxygen, blood sugar, or even body temperature.

Figure 5B:
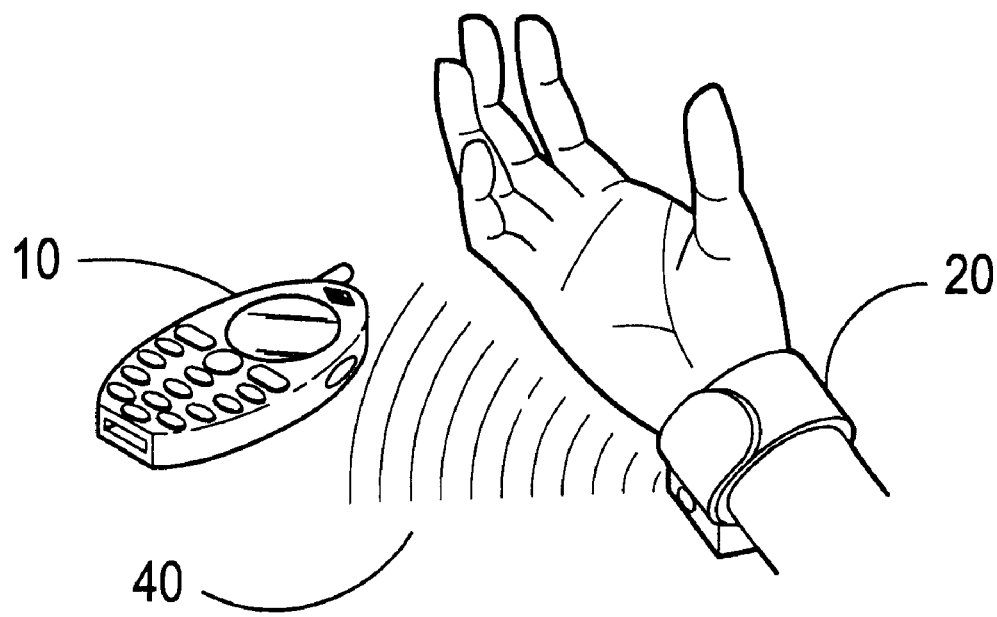

The signal emitted from the emitter 27 may be transmitted in form of direct wire connection 30 (shown in FIG. 5A) from an output end of the measurer 20 to an input end of the mobile phone set 10 or wireless 40 (shown in FIG. 5B).

From the above said, one thing is definitely sure that the mobile phone and the notebook computer will lead personal living intimately including management and monitoring health conditions. The merits of this invention may be summarized as the following:

1. The measured health data can be shown in the mobile phone display to remind a user of his body conditions.
2. The measured health data may be taken for therapy reference instead of oral statement that could possibly mislead illness situation.

Although, this invention has been described in terms of preferred embodiments, it is apparent that numerous variations and modifications may be made without departing from the true spirit and scope thereof, as set forth in the following claims.

What is claimed is:

1. A method of displaying human physical signals through mobile phone comprising the steps of:
   (a) detecting and measuring physical signals of a user by attaching a sensor of a measurer to in contact with a skin surface of said user;
   (b) converting said physical signals into electrical measured signals;
   (c) transmitting said electrical measured signals from a signal emitter of said measurer to a signal receiving module of a mobile phone;
   (d) converting said electrical signals to information signals adapted to be displayed on a phone display provided on said mobile phone, wherein the step (d) comprises the steps of:
      (d1) receiving said electrical measured signals form said measurer by a receiving circuit,
      (d2) decoding said received electrical measured signals by a decoder connected to said receiving circuit, and
      (d3) providing a standard level by a comparator connected to said decoder and comparing said electrical signals with said standard level to obtain said information signals; and
   (e) displaying said information signals on said phone display, wherein the step (e) further comprises the steps of:
      (e1) selecting a measuring mode in said mobile phone to activate said receiving circuit to receive said electrical measured signals which are then converted into said information signals which are displayed on said phone display; and
      (e2) providing an alert signal by said mobile phone when a phone call is received when said phone display is displaying said information signals.

* * * * *